(12) United States Patent
Parks et al.

(10) Patent No.: US 8,700,427 B1
(45) Date of Patent: Apr. 15, 2014

(54) WEB-BASED SYSTEM AND METHOD FOR HEALTHCARE COST MANAGEMENT

(75) Inventors: Christopher Andrew Parks, Franklin, TN (US); Robert Hendrick, Nashville, TN (US); Chris McIntyre, Nashville, TN (US); Matt Mueller, Nashville, TN (US); Michael L. Vucovich, Nashville, TN (US); Katrina Welty, Nashville, TN (US)

(73) Assignee: Change Healthcare, Inc., Brentwood, TN (US)

( * ) Notice: Subject to any disclaimer, the term of this patent is extended or adjusted under 35 U.S.C. 154(b) by 128 days.

(21) Appl. No.: 13/353,999

(22) Filed: Jan. 19, 2012

Related U.S. Application Data

(60) Provisional application No. 61/437,931, filed on Jan. 31, 2011.

(51) Int. Cl.
*G06Q 10/00* (2012.01)
*G06Q 50/00* (2012.01)

(52) U.S. Cl.
USPC ............................................................ 705/2

(58) Field of Classification Search
USPC ....................................................... 705/2, 3
See application file for complete search history.

(56) References Cited

U.S. PATENT DOCUMENTS

| | | | |
|---|---|---|---|
| 7,383,197 B1 | 6/2008 | Neuman | |
| 7,818,189 B2 | 10/2010 | Herzlinger | |
| 2002/0165738 A1* | 11/2002 | Dang | 705/3 |
| 2005/0182660 A1 | 8/2005 | Henley | |
| 2006/0136264 A1* | 6/2006 | Eaton et al. | 705/2 |
| 2007/0250352 A1* | 10/2007 | Tawil | 705/4 |
| 2008/0133511 A1* | 6/2008 | Schoenberg | 707/5 |
| 2010/0235183 A1 | 9/2010 | Firminger et al. | |

* cited by examiner

*Primary Examiner* — John Pauls
*Assistant Examiner* — Trang Nguyen
(74) *Attorney, Agent, or Firm* — Waddey Patterson; I. C. Waddey, Jr.; Gary L. Montle

(57) ABSTRACT

A web-based system of the present invention includes databases, processors and computer-readable memory media storing a computer program product is executable by the processor to perform functions of the invention. A claim is obtained regarding medical care services associated with a user and healthcare service data associated with the services. The healthcare service data for the obtained claim is compared to data for comparable claims in the system. Healthcare service options for the user are identified based on the compared data. A notification or alert regarding identified options is delivered to the user, and a second message upon request by the user provides details for obtaining or implementing the healthcare service options. A financial return report is subsequently generated based on input from the user corresponding to an actual difference in price between the services received and/or from comparison of subsequent claims.

17 Claims, 10 Drawing Sheets

My Potential Savings
$266

Prescriptions  $60
Medical        $50
Dental         $40
Other          $20

My Progress                    15%
What do I do next?

My Medical Plan Spending
Deductible ┆ Co-Insurance
           ▲
         $2,309 (you)

Your deductible has not been met. You will be responsible for the total cost. Tell me more.

Last Login: June 16, 2011

---

HYDROCODONE ACETAMINOPHEN
Information About Hydrocodone Acetaminophen and its Cost in Your Area TOTAL COST
$110-$145
How is this calculated?

This combination medication is used to relieve moderate to severe pain. Hydrocodone is a narcotic pain reliever (opiate-type) that acts of certain centers in the brain to give you pain relief. Acetaminophen is a non-narcotic pain reliever. HYDROCODONE/ACETAMINOPHEN - ORAL (hye-droe-KOE-done/a-SEET-a-MIN-oh-fen)... see details Dosage: [5MG - 500...▼]  Quantity: [30▶]

Prescription Options
1 - 4 of 14 results. Sort by Total Cost ▶

| | Total Cost | Rating |
|---|---|---|
| Walgreens Nashville Pharmacy<br>1234 Main Street, Nashville (.4 Miles)<br>800-555-1234 | $110 | ★★★★★ |
| Wal-Mart Supercenter<br>1234 Main Street, Nashville (.3 Miles)<br>800-555-1234 | $115 | ★★★★★ |
| Target West Nashville<br>1234 Main Street, Nashville (1.4 Miles)<br>800-555-1234 | $133 | ★★★★★ |
| CostCo #13567<br>1234 Main Street, Nashville (4.3 Miles)<br>800-555-1234 | $145 | ★★★★★ |

See More Options

\* Your Cost is what you can expect to pay based on your remaining deductible and/or co-insurance as of 5/4/2011. Total cost is determined using our proprietary cost savings engine. If you reach your deductible while purchasing this prescription, your cost will be less.

FIG. 5A

HYDROCODONE ACETAMINOPHEN
Information About Hydrocodone Acetaminophen and its Cost in Your Area TOTAL COST
$110-$145
How is this calculated?

This combination medication is used to relieve moderate to severe pain. Hydrocodone is a narcotic pain reliever (opiate-type) that acts of certain centers in the brain to give you pain relief. Acetaminophen is a non-narcotic pain reliever. HYDROCODONE/ACETAMINOPHEN - ORAL (hye-droe-KOE-done/a-SEET-a-MIN-oh-fen).... see details Prescription Options    Dosage: 5MG - 500... ▼    Quantity: 30 ▼

1 - 4 of 14 results. Sort by Total Cost ▼

| | Total Cost | Rating |
|---|---|---|
| Walgreens Nashville Pharmacy<br>1234 Main Street, Nashville (.4 Miles)<br>800-555-1234 | $110<br>$22 (Your Cost)<br>*$88 (Plan Cost)* | ★★★★★ |
| Wal-Mart Supercenter<br>1234 Main Street, Nashville (.3 Miles)<br>800-555-1234 | $115<br>$23 (Your Cost)<br>*$92 (Plan Cost)* | ★★★★★ |
| Target West Nashville<br>1234 Main Street, Nashville (1.4 Miles)<br>800-555-1234 | $133<br>$27 (Your Cost)<br>*$106 (Plan Cost)* | ★★★★★ |
| CostCo #13567<br>1234 Main Street, Nashville (4.3 Miles)<br>800-555-1234 | $145<br>$29 (Your Cost)<br>*$116 (Plan Cost)* | ★★★★★ |

See More Options

\* Your Cost is what you can expect to pay based on your remaining deductible and/or co-insurance as of 5/4/2011. Total cost is determined using our proprietary cost savings engine. If you reach your deductible while purchasing this prescription, your cost will be less.

My Potential Savings
$266

Prescriptions   $60
Medical   $50
Dental   $40
Other   $20

My Progress   15%
What do I do next?

My Medical Plan Spending
Co-Deductible | Insurance
$2,789 (you)

Your deductible has not been met. You will be responsible for the total cost. Tell me more.

Last Login: June 16, 2011

*FIG. 5B*

My Potential Savings

$266

- Prescriptions $60
- Medical $50
- Dental $40
- Other $20

My Progress 15%

What do I do next?

My Medical Plan Spending

Deductible : Co-Insurance $2,309 (you)

Your deductible has not been met. You will be responsible for the total cost. Tell me more.

Last Login: June 16, 2011

---

How to Save $100 on Your Lipitor

Step 1: Select a New Pharmacy > Step 2 > Step 3

Your Lipitor prescription at Rite Said cost $1,400 in the past 12 months. Switch to one of the pharmacies below and save up to $100 per year.

Select a New Pharmacy                                         Map View

Sort by Total Cost ▼                          Total Savings      Rating

- ● A. Walgreens Nashville Pharmacy           $100         ★★★★★
  1234 Main Street, Nashville (.4 Miles)
  800-555-1234

- ○ B. Wal-Mart Supercenter                   $100         ★★★★★
  1234 Main Street, Nashville (.3 Miles)
  800-555-1234

- ○ C. Target West Nashville                  $90          ★★★★★
  1234 Main Street, Nashville (1.4 Miles)
  800-555-1234

- ○ D. CostCo #13567                          $85          ★★★★★
  1234 Main Street, Nashville (4.3 Miles)
  800-555-1234

[ No Thanks ]   [ Next ]

\* Total Savings is the maximum amount you and your plan can save at this location. Your savings is calculated based on your remaining deductible and/or co-insurance as of 5/4/2011.

*FIG. 6A*

WEB-BASED SYSTEM AND METHOD FOR HEALTHCARE COST MANAGEMENT

CROSS-REFERENCES TO RELATED APPLICATIONS

This application claims benefit of the following patent application(s) which is/are hereby incorporated by reference: U.S. Provisional Patent Application No. 61/437,931, dated Jan. 31, 2011.

BACKGROUND OF THE INVENTION

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

The present invention relates generally to a system and method for managing healthcare costs. More particularly, this invention relates to a web-based system which effectively tracks healthcare services, compares prices for comparable services, and actively reaches out to and informs users about the financial implications of services.

The price of healthcare services (including but not limited to therapies, prescriptions, durable medical good, dental services, and any other medical services recognized by health-related services) is difficult to ascertain for providers and for patient-consumers. There are over 12,000 different types of services, therapies and products that can be billed and over 19,000 different prescriptions. Compounding the problem, the price is often nebulous or obscured through variations in network contracts, variations in reimbursements within networks for the same service, benefit plan design and many other factors. Providers often provide services and prescribe services without knowing the financial burden their patients will incur, just as patient-consumers often lack perspective on the financial burden they are incurring prior to receiving services.

Healthcare providers work under many different network contracts. There are often very significant variations in contracted reimbursement rates from one network to the next. In addition, those contracts are subject to change at renewals, may be tied to external pricing mechanisms (i.e. Medicare/Medicaid rate) or may be a percentage of a charge or part of a bundled set of services or part of a capitated contract (a plan that allows payment of a flat fee for each patient treated). And within the network, one provider may be compensated at a different rate than another provider with the same specialty for the same service. Extending the issue beyond the provider's lack of insight into their own practice, those providers likewise have no insight into the price of services they prescribe or they refer.

For the patient-consumer, plan benefit design adds another wrinkle of uncertainty to the price. Benefit design determines which services are covered or not, which providers are in network or out, and how the burden of payment is distributed—all of which can impact the price of healthcare for the patient-consumer. In addition, the complexity of medical terminology and practices around coding and billing puts patient-consumers at an even greater disadvantage since they are generally uneducated on the clinical aspect that often distinguishes services.

The result is an environment in which the patient depends upon the physician to advise them, but the provider is not able to do so with reasonable perspective on the associated costs. As a result, it is virtually impossible for patients or their providers to determine costs prior to treatment, and therefore the ability to consider financial implications of care are compromised.

It would therefore be desirable to provide a system and method which could provide information as required for providers and/or patient-consumers in order to be able to consider the financial implications of the care they prescribe or receive.

BRIEF SUMMARY OF THE INVENTION

In accordance with one aspect of the present invention, a web-based system acts on behalf of the user (provider and/or the patient-consumer) to track services, compare prices for comparable services, and actively reach out to and inform the user about the financial implications of services. The system may be extended to identify more cost effective options.

In another aspect, the information is delivered in digital format via web site, text message, e-mail, app or other electronic means. The information may further be delivered by more traditional printed means. The information may also be delivered to an intermediary who can be prompted to reach out personally with the information to deliver the information.

Another unique aspect of the system is the integrated educational component. A user receives highly customized information about the specific actions required in order to change how they are receiving services. In addition, the system tracks the financial return to the user through utilization of the system.

In a particular embodiment of the present invention, a web-based system includes a host database, user interface, processor and computer-readable memory medium each functionally linked on one or more host servers and coupled to a communications network. The memory medium includes program instructions executable by the processor to perform the various steps in an embodiment of a method in accordance with the invention. A claim is obtained from a registered user regarding healthcare services, the claim including healthcare service data associated with the services. The healthcare service data for the obtained claim is compared to healthcare service data for comparable claims which are stored in the database. Healthcare service option(s) for the user are identified based at least in part on the compared data. A notification or alert for the identified option is delivered to the user, or otherwise posted on a web page or other interface associated with the system. Upon receiving a user request for further information or otherwise approving or selecting an option, a second message provides the user with details for obtaining or implementing the approved or selected healthcare service option. A financial return report is subsequently generated via a user interface based on input from the user corresponding to an actual difference in price between the services received.

In another embodiment, the claims may be received by the hosted system from a healthcare plan administrator on behalf of a plan participant, wherein the system generates healthcare service options for the plan participant and contacts the participant either directly or through the administrator.

In another embodiment, where the plan participant is not a registered user of the host system, the system may determine comparable claims and identify healthcare service options based only on healthcare plan details for a first claim, but subsequently prompt the participant to register as a user of the host system or otherwise provide user-specific details which may be used with respect to subsequent claims.

BRIEF DESCRIPTION OF THE SEVERAL VIEWS OF THE DRAWINGS

FIGS. 5A and 5B are modified screen shots representing a first exemplary graphical user interface field according to the present invention wherein a user is in a deductible stage and a co-insurance stage of an associated plan, respectively.

FIGS. 6A and 6B are modified screen shots representing a second exemplary graphical user interface field according to the present invention wherein a user is in a deductible stage and a co-insurance stage of an associated plan, respectively.

DETAILED DESCRIPTION OF THE INVENTION

Figure 1:
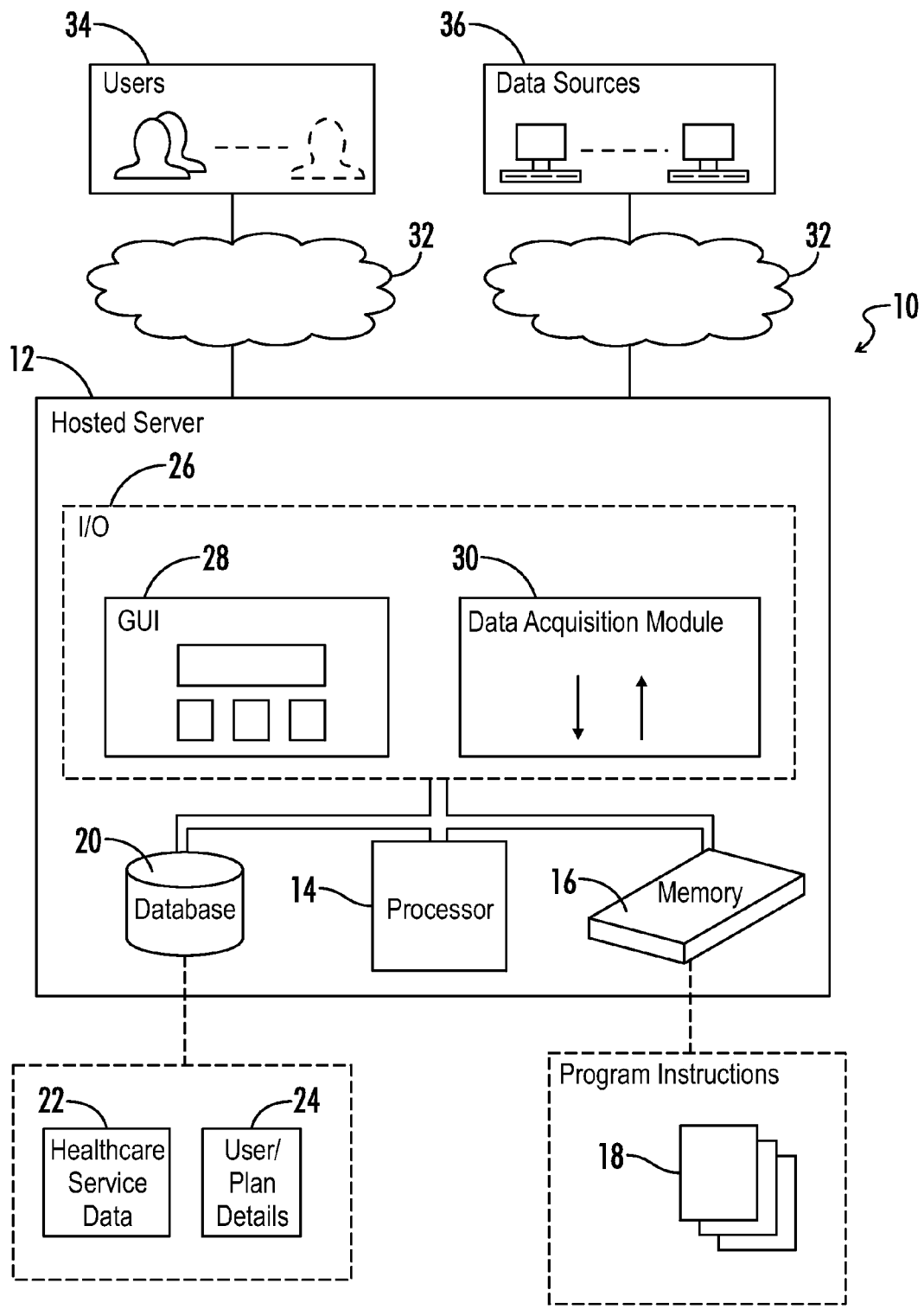
FIG. 1 is a block diagram representing an embodiment of a system according to the present invention.

Referring generally to FIGS. 1-8, systems and methods in accordance with the present invention are provided herein for acting on behalf of a user (provider and/or the patient-consumer) to track healthcare-related services, compare prices for comparable services, and actively reach out to and inform the user about the financial implications of services. Where the various figures may describe embodiments sharing various common elements and features with other embodiments, similar elements and features are given the same reference numerals and redundant description thereof may be omitted below.

Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in" and "on." The phrase "in one embodiment," as used herein does not necessarily refer to the same embodiment, although it may. Terms such as "providing," "processing," "supplying," "determining," "calculating" or the like may refer at least to an action of a computer system, computer program, signal processor, logic or alternative analog or digital electronic device that may be transformative of signals represented as physical quantities, whether automatically or manually initiated.

In various embodiments such as that represented in FIG. 1, a host system 10 of the present invention may have a web-based network structure residing on one or more host servers 12 and which is effective to receive and transmit data over a communications network 32 with one or more computers on remote servers associated with various separate users 34. A user 34 may include for example individual healthcare providers, a group of healthcare providers, a healthcare patient/consumer/recipient/caregiver or may refer instead to any other entity such as a plan administrator that may benefit from the cost management services of the present invention. The system 10 may further be effective to receive and transmit data over the communications network 32 with various third party information sources 36 such as for example may provide medical services data as needed or otherwise useful for performing the various stated functions of the present invention.

The term "web-based system" as used herein may, unless otherwise stated, refer generally to a platform effective to implement web-transitory functions, whether browser-based or otherwise. In other embodiments, the host system may within the scope of the present invention include other computer-implemented platforms and networks known to those of skill in the art which are not web-based.

The term "communications network" as used herein with respect to data communication between two or more parties or otherwise between communications network interfaces associated with two or more parties may therefore refer to any one of, or a combination of any two or more of, telecommunications networks (whether wired, wireless, cellular or the like), a global network such as the Internet, local networks, network links, Internet Service Providers (ISP's), and intermediate communication interfaces.

The term "healthcare services" as used herein may refer to any goods and/or services which may be covered under a healthcare plan and for which one of skill in the art may appreciate that cost management solutions within the scope of the present invention may apply. Such services may include but are not limited to therapies, pharmaceutical services, prescriptions, medical procedures, durable medical goods and equipment, dental services, counseling, and/or other equivalents which may benefit the health of an associated user as may be appreciated by those of skill in the art.

A host system 10 in accordance with the present invention may include one or more data processors 12, an input/output (I/O) module 26 and a computer-readable memory medium 16 containing a computer program product 18 executable by the one or more data processors 12 using techniques as are well known in the art. In some embodiments (not shown), a single memory medium 16 may be provided which is effective to store the computer program 18 and also any data which is received and used in relation to the program 18. In other embodiments a plurality of memory media 16 including that containing the computer program 18 as well as one or more databases 20 or equivalent storage entities 20 may be provided and functionally linked to collectively perform the functions of the system 10 as described herein. It may further be understood that more than one type of memory media may be used in combination to conduct processor-executable software, instructions or program modules from a first memory medium upon which the software, instructions or program modules initially reside to a processor for execution.

In various embodiments of the present invention, the database 20 is provided and effective to store medical services data 22 associated with one or more claims which have been received and accessed for medical services data (as further described below), and further to store details 24 associated with the various registered users, healthcare plans, etc., as further described below.

The computer program 18 in various embodiments may contain various instructions executable from a single program to perform functions of the present invention as described below. The program instructions may further include or otherwise define a plurality of software modules executable by the data processor 12 to perform the functions. In various embodiments the system 10 may include a plurality of servers upon which separate components reside but are electronically coupled, or upon which identical copies of the various components reside for more rapid and efficient use of resources.

The term "processor" as used herein may refer to at least general-purpose or specific-purpose processing devices and/or logic as may be understood by one of skill in the art, including but not limited to central processors, parent processors, graphical processors, media processors, and the like.

The I/O module 26 may in various embodiments such as exemplified in FIG. 1 may include either or both of computer program instructions 18 effective to generate a graphical user interface 28, and computer program instructions 18 further defining a data acquisition module 30. The user interface 28 as referred to herein may include a host website with one or more web pages and various associated graphical or audiovisual elements such as for example icons, buttons, check boxes, text boxes, sounds, videos and the like. The user interface 28 may in certain embodiments be generated remotely on a remote computing device such as for example a smart phone when implemented in the context of a mobile application associated with the host system 10, and communicatively linked to the server 12 via the communications network 32. The data acquisition module 30 may in various embodiments be implemented to actively collect online information related to for example particular third-party medical service providers, and/or may more passively receive information submitted to the system from third-party providers, and/or may acquire data directly from users via for example data entry fields generated within or as linked from the user interface 28. The data acquisition module 30 may be executed by the processor on a predetermined schedule to actively request or acquire data, or may be executed upon a predetermined trigger such as for example an identified user action or upon identifying a submission via the communications network to the server from a third party provider.

Figure 2:
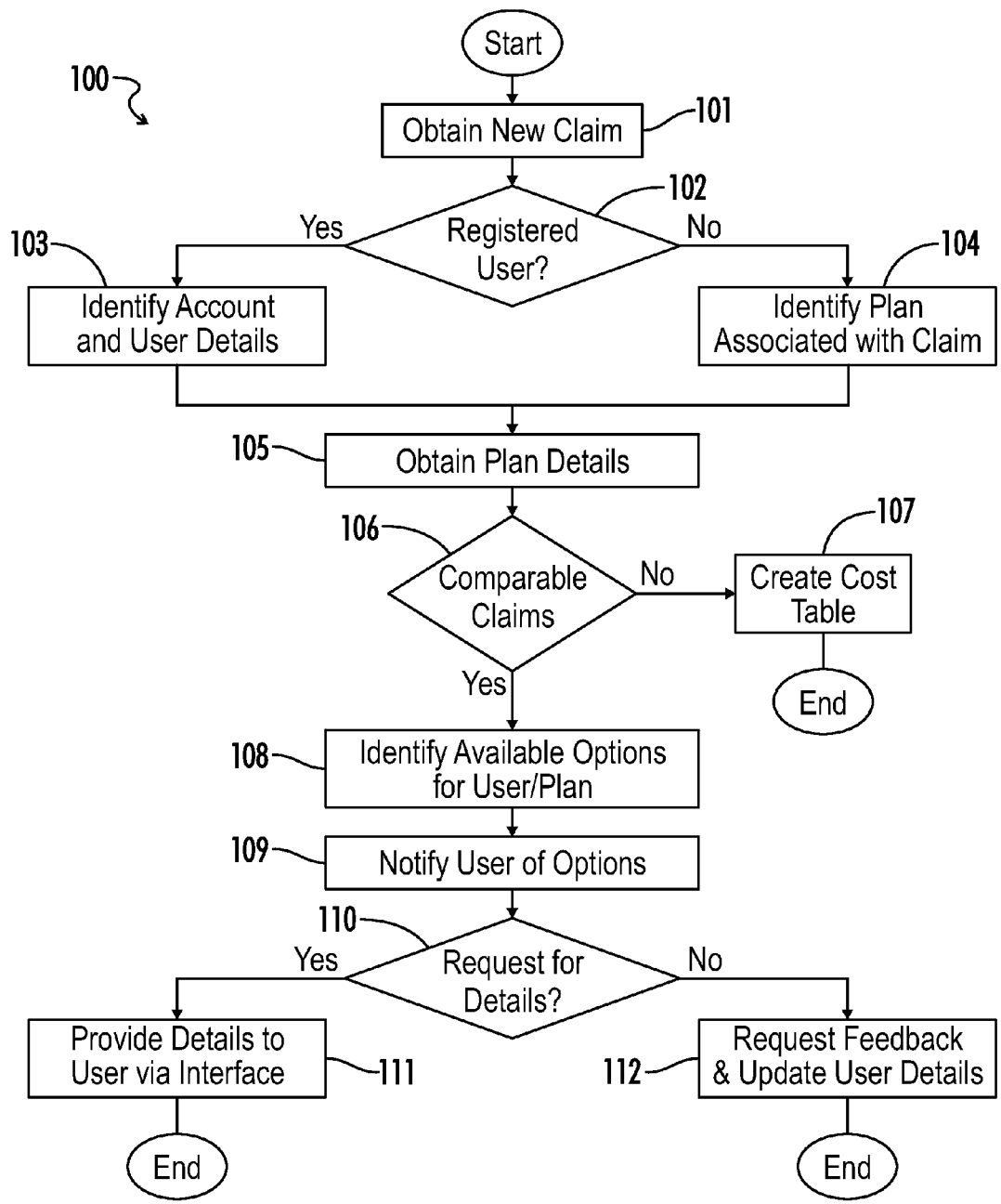
FIG. 2 is a flowchart representing an embodiment of a method according to the present invention.

Referring now to FIG. 2, an embodiment of a web-based method 100 may be described in association with the host system represented in FIG. 1 for acting on behalf of a user (provider and/or the patient-consumer) to track services, compare prices for comparable services, and actively reach out to and inform the user about the financial implications of services. The presence of any steps in the method 100 as represented in FIG. 2 may serve as sufficient disclosure insofar as they may be understood by one having ordinary skill in the art. Further, the description of a step in accordance with an embodiment of the present invention is not to imply that the step is necessary to each and all embodiments unless otherwise explicitly stated. Even further, various embodiments are anticipated within the scope of the present invention which may include combinations of elements across the various figures herein provided.

In the following description, the particular "user" refers to a consumer or recipient or caregiver of healthcare services for explanatory purposes, but this does not limit the use of the term "user" insofar as medical care providers may fall within the scope of this term in various alternative embodiments, namely, a person or entity for whom medical care (services, products, prescriptions) is/are provided. Accordingly, a first user receives healthcare services for which a new claim is generated for the purpose of the provider receiving reimbursement and/or medical record documentation. The user may typically have access to some but not necessarily all healthcare service data associated with the new claim.

The method 100 begins by obtaining a new claim associated with healthcare services (step 101). The new claim may be obtained in various embodiments from an end user such as a patient or consumer of the services that has previously registered with the host system, or from an administrator of a healthcare plan associated with the patient or consumer of the services.

The term "new claim" as used herein may refer to at least the initial access to documentation of medical care provided for the user for the purpose of receiving or attempting to receive reimbursement for the provision of the service(s). A "new" claim in various embodiments may in fact include a known upcoming service related to previous services for which further action is required or scheduled, for example where an initial claim includes a prescription which is scheduled to be renewed or a medical service which requires subsequent follow-up procedures or check-ups. Likewise, the term "previous claim" as used herein may refer to at least a previously new claim that has already been processed through the host system, or a claim that has never been specifically processed through the host system but embodies healthcare service data obtained, collected or extracted from various third-party data sources.

In various embodiments, the method includes determining if the user (i.e., consumer of healthcare services or participant in the associated healthcare plan) is a registered user of the system (step 102). If so (i.e., "yes" in response to the query in step 102), an account for the user is identified in a system database and user details may be further identified or extracted for use in further steps (step 103). If the user is not registered with the system (i.e., "no" in response to the query in step 102), a healthcare plan associated with the new claim or with the administrator submitting the new claim to the system may be identified (step 104). Plan details may further be identified from the associated healthcare plan or from the user account if the user was previously registered (step 105). In various embodiments the plan details may be relevant in determining available or otherwise preferred service providers, cost thresholds, deductable information, etc.

In an exemplary embodiment, a data acquisition process may within the scope of the present invention may begin by obtaining, receiving or otherwise importing a raw data file including eligibility, dental or medical claims, pharmacy claims, and any other required data elements gathered from for example an internal server (for example SSH File Transfer Protocol or SFTP) or retrieved from an external file drop location associated with the relevant vendor. Dynamic SQL may be used to determine how and where the file is imported based on the path and the filename. The system verifies that counts on each file match with control totals.

The raw data may then be loaded to the system database, wherein individual files are loaded to dedicated tables and remain in a source-specific format. The underlying data may be audited to verify that the new data is in the expected format and that all required elements are present, and completed to establish trending information for items such as active member count, claims volumes, claims costs, etc.

The raw data may then be converted to a format more generally associated with the host system, wherein source-specific values for items such as for example provider specialty, place of service, relationship codes are converted into standard host-specific values. This step may include member to claim matching, elimination of duplicate entries, claim adjustment handling, provider matching based on provider identifiers and demographics, and the like.

In certain embodiments, the raw data conversion step may be unnecessary, where for example the source data is initially provided in a standard format which is compatible with that of the host. The host system may facilitate such data extractions by providing for example a template, data formatting instructions, data delivery schedules, etc.

The converted data may then be provided for use in various cost calculation engines or otherwise stored in the host database. Reconciliation may be completed with respect to previously stored application data and new/updated members/claims/costs sent to the application database. Another audit may be performed on reconciliation results to verify that all changes were posted appropriately.

Returning to the method of FIG. 2, upon receiving or otherwise obtaining the new claim and the associated healthcare service data, the data is further assessed to see if the new claim is comparable to previous claims which are stored in the database of the host system (step 106). The term "comparable" as used herein with relation specifically to new and previous claims means unless otherwise stated that provider specialty, service code (which may be defined by title, description, CPT, HCPCS, NDC, prescription name, etc.), network, etc., are substantially the same or otherwise within a reasonable relationship to one another. "Comparable" may further be extended to include geographic location as a variable or as a fixed value. In an embodiment, what constitutes a comparable claim may be more specifically defined or otherwise narrowed in scope by a user or plan administrator and stored in the database in association with the user or associated plan.

If the new claim is not comparable to previous claims (i.e., "no" in response to the query in step 106), the system may create a cost table for the new claim, and store the created cost table for future use (step 107). The term "cost table" as used herein may refer to at least the inferred or calculated cost for medical care (which may be defined by title, description, CPT, HCPCS, NDC, prescription name, etc.) by a given provider. The cost table may in certain embodiments be insurance network specific.

If the new claim is comparable to previous claims for which there is an existing cost table (i.e., "yes" in response to the query in step 106), then the new claim may be compared by the system with the previous claims for the purpose of identifying potentially available and/or preferred healthcare service options based for example on any combination of user details, plan details, healthcare service data (aggregated or individually assessed), and/or any other relevant factors as may be determined by those of skill in the art (step 108).

In an embodiment, the new claim is factored into a recalculation of the comparable cost table and its associated confidence metric. The term "confidence metric" as used herein may refer to at least a value that indicates the level of certainty in the accuracy of the cost table. Examples of factors to be used in the confidence metric may include without limitation data quality, consistency and age, in any combination or altogether.

Figure 3:
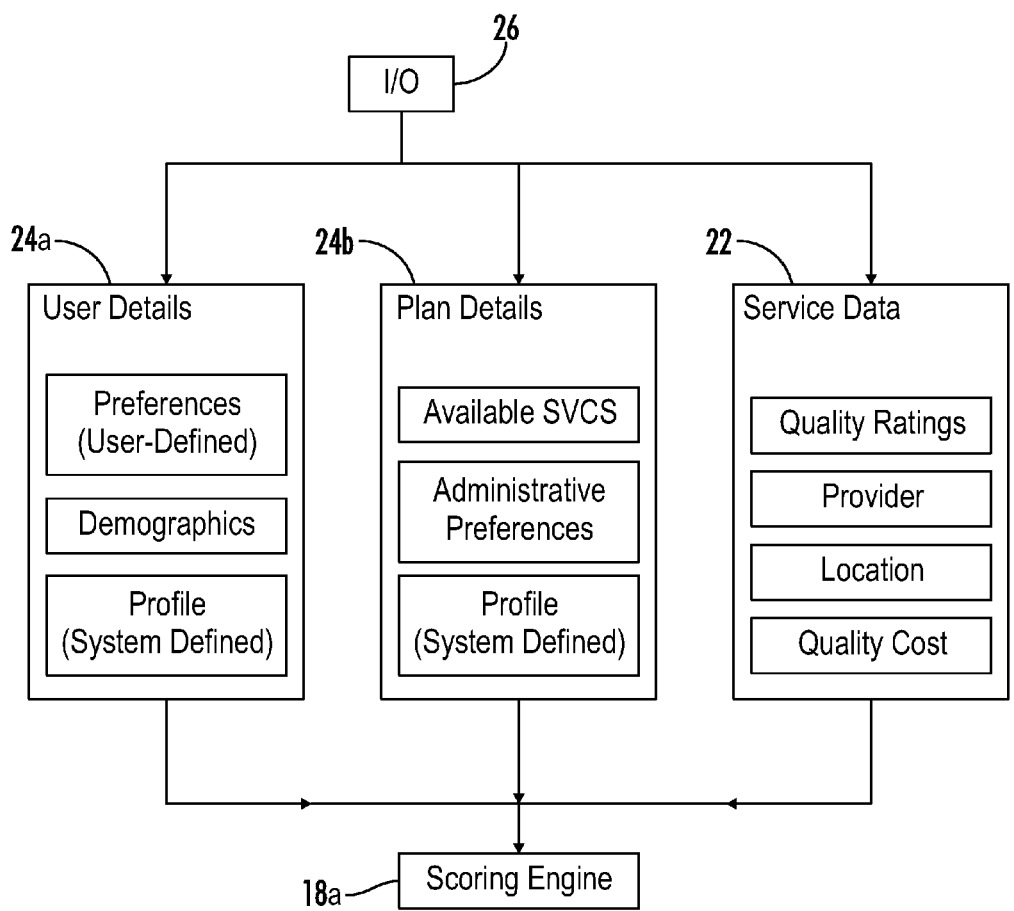
FIG. 3 is a block diagram representing an embodiment of a healthcare service option scoring engine in a system according to the present invention.

One exemplary process for identifying or otherwise determining the availability of alternative healthcare service options may be to merely filter out options which do not meet threshold requirements as predetermined and stored in the system. Referring to FIG. 3, the system may include one or more databases 20 or database fields 24 within which some combination of user details 24a for the relevant user/consumer of the services of the new claim, plan details 24b for a relevant healthcare plan of the user, and/or the healthcare service data 24c for the new claim and any claims which have been identified previously as being comparable. The relevant data, having been previously collected via the I/O module(s) 26 and stored within the system databases 24, may be extracted in step 108 for use in a scoring engine or equivalent program module and processed according to an associated algorithm for scoring, ranking, filtering, or otherwise identifying potential options.

Exemplary user details 24a may include user-defined preferences such as for example a minimum amount of cost savings below which the user would prefer not to receive notification of alternative or additional service options, a maximum distance the user is willing to travel, preferred brands, preferred service providers, etc. Demographics for the user may be stored and processed against the user-defined preferences, such as for example location-based filters where a change in address for the user would be applied with respect to the maximum distance the user is willing to travel. Another demographic example may be where health-related data associated with the user may be stored and for example relied upon to filter out options which are contra-indicated with respect to an otherwise available option, or which otherwise conflict with standing medical orders or suggestions. Additional user details may include those associated with a profile generated by the system based on previous user responses or monitored user activity across the system platform or any one or more third party platforms which the host system may be capable of tracking.

A scoring engine according to an embodiment of the present invention may for example include a weighting factor that for example applies a higher score to providers that have been visited (or web pages associated with those providers that have been visited) by the user within a predetermined time period, or otherwise diminishes the relevance for options which have been visited or identified by the user as time passes. In an embodiment the scoring engine may ascribe greater weight at all times to specific user-defined preferences and demographics, while applying a relatively small amount of weight initially to ambiguous inferences to be made from the user preferences but gradually over time applying a greater weight to a system-generated profile as more information is obtained.

Exemplary plan details 24b may include specific limitations as to the providers or type of providers, covered medications, covered services, etc. Further, even where specific limitations are not applied which may be utilized as binary filters with regards to a specific option, administrative preferences may be provided and stored such as for example a preferred list of providers, medications, services, etc. In various embodiments the scoring engine may thereby weight any scores or rankings for otherwise available options according (in part) to whether or not they are associated with one or more administrative preferences. Additional plan details may include those associated with a profile generated by the system based on for example previous activity with respect to the particular plan, whether by the same user or other users as recorded and processed using the system, and whether by the same plan administrator or other entity utilizing the system of the present invention. Activity by other participants in the plan may for this purpose be monitored across the system platform or any one or more third party platforms which the host system may be capable of tracking, and such activity relied upon to generate the plan profile and applied with respect to options for the registered user in the given example.

With regards to both of the user profile and the plan profile as noted above, these descriptions are merely exemplary, and in various embodiments within the scope of the present invention such system-generated profiles, filters, and machine-learning features may be excluded, disabled or otherwise minimized in the identification of healthcare service options. Depending on the type of scoring (e.g., where only a filtering mechanism is applied to the comparable claims based strictly on plan availability and user preferences) these profiles may in fact be redundant or otherwise undesirable and may therefore be omitted.

Exemplary healthcare service data 24c which may be relied upon or otherwise utilized by the scoring engine against the user details and/or plan details as described above, may include without limitation any combination of the service provider, the location, the brand or type of services, and/or quality ratings for the particular brand, provider, location, etc., as directly provided by users of the system with regards to previous experiences or otherwise as derived from third party sources.

Once one or more options have been identified in step 108, the method proceeds to step 109 and notifies the user of the options. For example, in a case where the user preferences merely recite a desire to identify any options that would reduce the costs of services without other filters or qualifications, and for a given new claim there is a lower price healthcare service option identified in the cost table, an alert may be generated and queued for the user. The term "price" as used herein may refer to any monetary figure that allocates the price of medical care either in whole or in part including but not limited to provider charge, total reimbursement to the provider, negotiated rate, patient responsibility, insurer responsibility, co-pay amount, etc. The term "alert" as used herein may refer to at least an electronically generated communication conveying the existence of a more cost-effective healthcare service option. In various embodiments, alerts may be delivered via a web site, e-mail, text, mobile software application, or other appropriate electronic/digital techniques as are well known in the art. Alternatively, within the scope of the present invention alerts may further be delivered via physical techniques (i.e., mail, paper, etc.), or may be served to an intermediary for manual delivery.

The alert (notification) may be required to meet predetermined parameters including but not limited to frequency, savings values, delivery method, etc. If those parameters are met or are not set, the alert may be delivered to the user within the set parameters (e.g., frequency, date, time, etc.) for delivery. Additionally, if the new claim represents the lowest price option for healthcare services in a cost table, other claims may also be reassessed and a new alert for other claims related to the cost table may be generated by the system.

In various embodiments, a claim frequency for new claims may be calculated and a reminder queued within the system. The parameters for the date/time of delivery of the reminder may therefore be predetermined and set within the system. The term "claim frequency" as used herein may refer to at least a calculated rate at which a claim tends or may otherwise be demonstrated to occur. The term "reminder" as used herein may refer to at least an electronically generated communication that anticipates the upcoming need for a service or a prescription for which exists a more cost-effective option. Reminders may be delivered via a web site, e-mail, text, mobile software application, or other appropriate electronic/ digital techniques as are well known in the art. Alternatively, within the scope of the present invention reminders may further be delivered via physical techniques (i.e., mail, paper, etc.), or may be served to an intermediary for manual delivery.

The method 100 then may generally await further action by the user (step 110). If the user affirmatively selects or otherwise requests additional information regarding one or more of the identified options (i.e., "yes" in response to the query of step 110), the user may in certain embodiments be sent additional message(s) or otherwise prompted with appropriate actions to take and the required information in order to realize the more cost-effective options for medical care. This information may include information both readily available to the user and/or information not typically available to the user.

If the user does not respond, in various embodiments the system may return to step 109 and initiate additional alerts and/or reminders (not shown). The system may in an embodiment send only a fixed number of alerts and/or reminders, after which the particular iteration of the method 100 is terminated and no additional alerts and/or reminders are sent regarding the particular notification. The system may further be programmed to execute only a fixed number of iterations of the method 100 with respect to a particular user, wherein failure by the user to acknowledge any of the alerts and/or reminders may cause the system to terminate future actions with respect to the user or generate a notice of potential termination of such future actions to the user and/or plan administrator.

If the user responds negatively to the alert (i.e., "no" in response to the query of step 110), the user may in certain embodiments be prompted for the reasons for responding negatively, and the response including the relevant reasons logged within the system.

Figure 4:
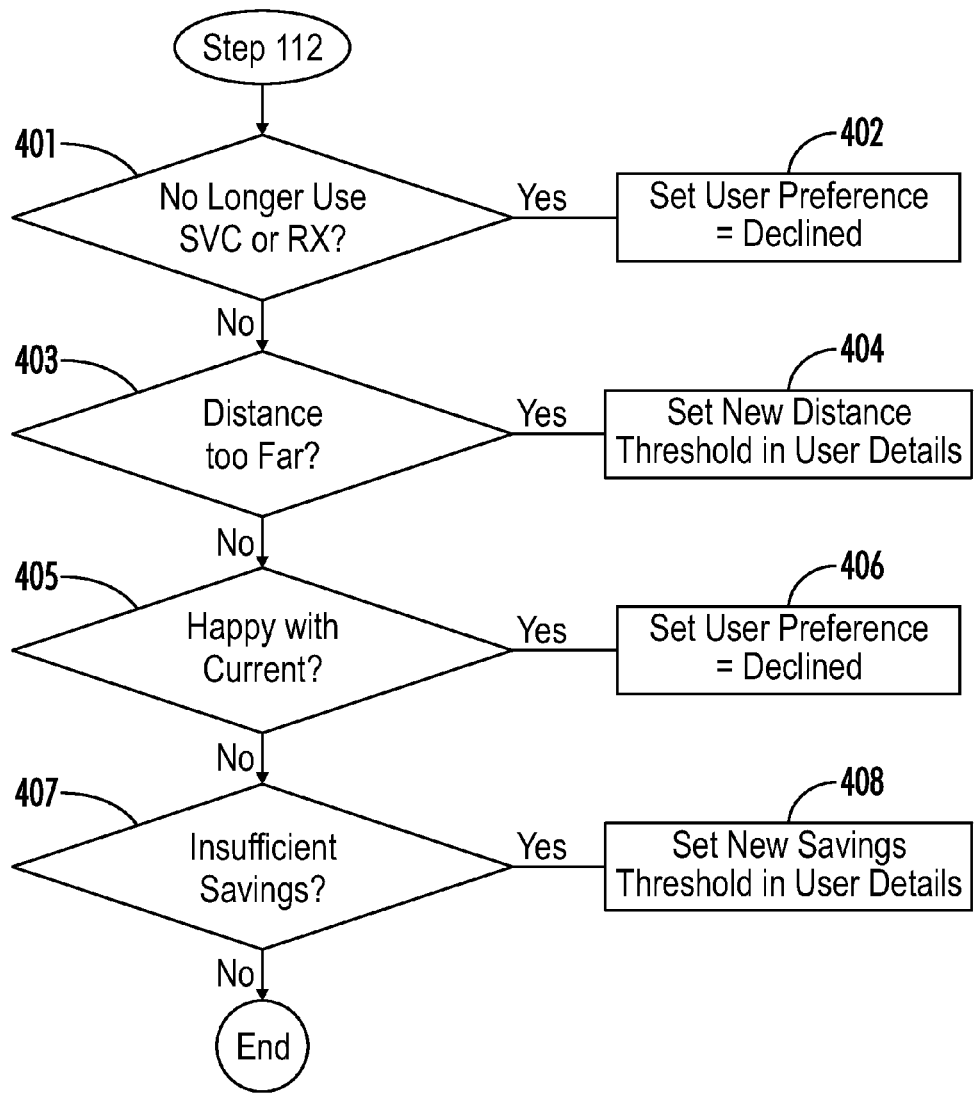
FIG. 4 is a flowchart representing an embodiment of a feedback request process pursuant to declined options in the method of FIG. 2.

Referring to FIG. 4, in a particular exemplary embodiment a declined options feedback module may be executed pursuant to a negative response by the user. The module may prompt the user as to whether or not the options were declined because they no longer use the particular service, the service provider, or the brand of medication, etc. (401), in which case the user details may be updated to indicate that comparable options were declined (402) so as to adjust subsequent scoring engine results accordingly. The module may prompt the user as to whether or not the options were declined because the distance was too far for the user to travel to leverage one or more of the service options (403), in which case the user details may be modified to adjust a threshold distance (404), or to simply cause the scoring engine to weight the distances in future calculations accordingly, and without automatically rejecting services having an equivalent distance. The module may prompt the user as to whether or not the options were declined because they are happy with their current provider, brand, service, etc. (405), in which case the user details may be modified to cause the scoring engine to weight that particular component in future calculations accordingly (406). The module may prompt the user as to whether or not the options were declined because there were insufficient cost savings (407), in which case the user details may be modified to adjust a threshold cost savings (408), or to simply cause the scoring engine to weight the cost savings in future calculations accordingly, and without automatically rejecting services having an equivalent cost savings.

In various embodiments, the system may include a savings determination module for identifying direct, extended or prospective savings in accordance with identified options presented to a user or services which have actually been used by a user. "Direct savings" may be for example those which are determined based on direct user feedback, extrapolated from previous iterations of the same service from the same provider, or associated with a coupon, rebate or other verifiable and reliable source of savings. "Extended savings" may be for example those which are determined in association with alternative providers of a same or analogous service, expected cost data from new claims/services offered by old or new providers, modifications to previous direct savings according to revisions in the underlying data (e.g., user details or plan details), and the like. "Prospective savings" may be for example those which relate to information from the service providers rather than the users themselves, and are determined to be potentially available and associated with services that have not yet been acted upon, but are outside of the scope of direct or extended savings and typically would take less priority in the weighting process. The different types of savings may be associated with respective weightings, displays or other effective distinctions within the scope of the present invention for identifying future options or generating reports.

If the new claim is associated with a previously created alert, in various embodiments the new claim may be compared with the claim which prompted the creation of the alert. The variation between the payment amounts between the two claims may be logged for additional calculations that are used to provide feedback to the user and other authorized parties with an interest in the interaction of the user with the system.

Alternatively, in various embodiments the system may receive or otherwise acquire input from the user regarding the costs of the healthcare services associated with an alert having previously been provided by the system, in which case the system may generate a financial return report corresponding to an actual and verifiable difference in price between the services received prior to the alert and those received afterwards by the user.

Referring now to FIGS. 5-8, various display screens are represented in association with web pages generated according to an exemplary interface of the present invention. Equivalent displays or displayable information may further be generated with respect to a mobile application for a smart phone or other equivalent interface platforms within the scope of the present invention. Various additional display screens may be understood as being further generated for the interface of the present invention but are nonetheless omitted in the figures shown, without any implication or understanding to be drawn from such omissions, such displays including for example user login screens, data entry fields for user preferences, etc.

FIGS. 5A and 5B represent a first exemplary display screen 50 for a prescription detail page as accessed by the user from for example a cost lookup feature. A first area or portion 52 of the interface 50 may indicate the current deductible status for a relevant healthcare plan, options of which may include without limitation Deductible, Co-Insurance and Covered. In the example shown, the user is in the deductible phase. A second area or portion 54 of the interface 50 includes the total, all-in cost for the recited service or prescription of the new claim. A third area or portion 56 of the interface 50 provides the total cost for one or more identified service or prescription options, as scored/ranked for example from lowest to highest while still being available (i.e., lower than the high end of the recited prescription cost). The total cost displayed is variable. In the example shown in FIG. 5A, since the user is still in their deductible phase, they will pay the full price for the prescribed medication without any plan contribution. In another example as shown in FIG. 5B, wherein the user is in their co-insurance phase, the full total cost may be shown but further broken down with respect to "user cost" as well as the "plan cost" according to for example an 80/20 arrangement. In yet another example (not shown), wherein the user is fully covered, the total cost of the service is generated but there would now be an indicator of the user cost being 0$ while the plan cost would be 100% of the total cost. A disclaimer may be provided (e.g., along the bottom of the represented interface 50) to indicate how the various costs are in fact determined.

Figure 6B:
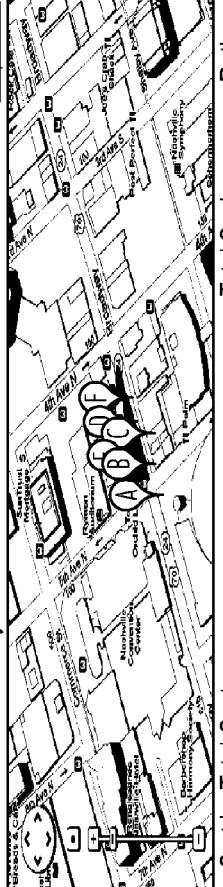

FIGS. 6A and 6B represent a second exemplary display screen 60 for a savings detail page within the scope of the present invention. This interface 60 may be generated for example in response to a user query or selection regarding details of a particular identified option. In the example shown, the user has accessed the page for the purpose of learning how to reduce costs (e.g., save $100 per month) on their prescription (e.g., for Lipitor), with respect to a particular provider/pharmacy (e.g., Rite Aid) having a particular cost over the past year (e.g., $1400). A portion 62 of the interface 60 is dedicated to displaying the available and identified options. One distinction with respect to the previous display 50 is that the identified options may be listed according to the total savings rather than item cost, and indications provided relating to which party the savings will go to rather than who will pay the cost. As represented in FIG. 6A, where the user is in the deductible stage, all of the savings will go to the user. As further represented in FIG. 6B, where the user is in the co-insurance stage, a portion of the savings will go to the user and the remaining savings will go to the plan administrator commensurate with the plan details (e.g., an 80/20 co-insurance plan).

Figure 7:
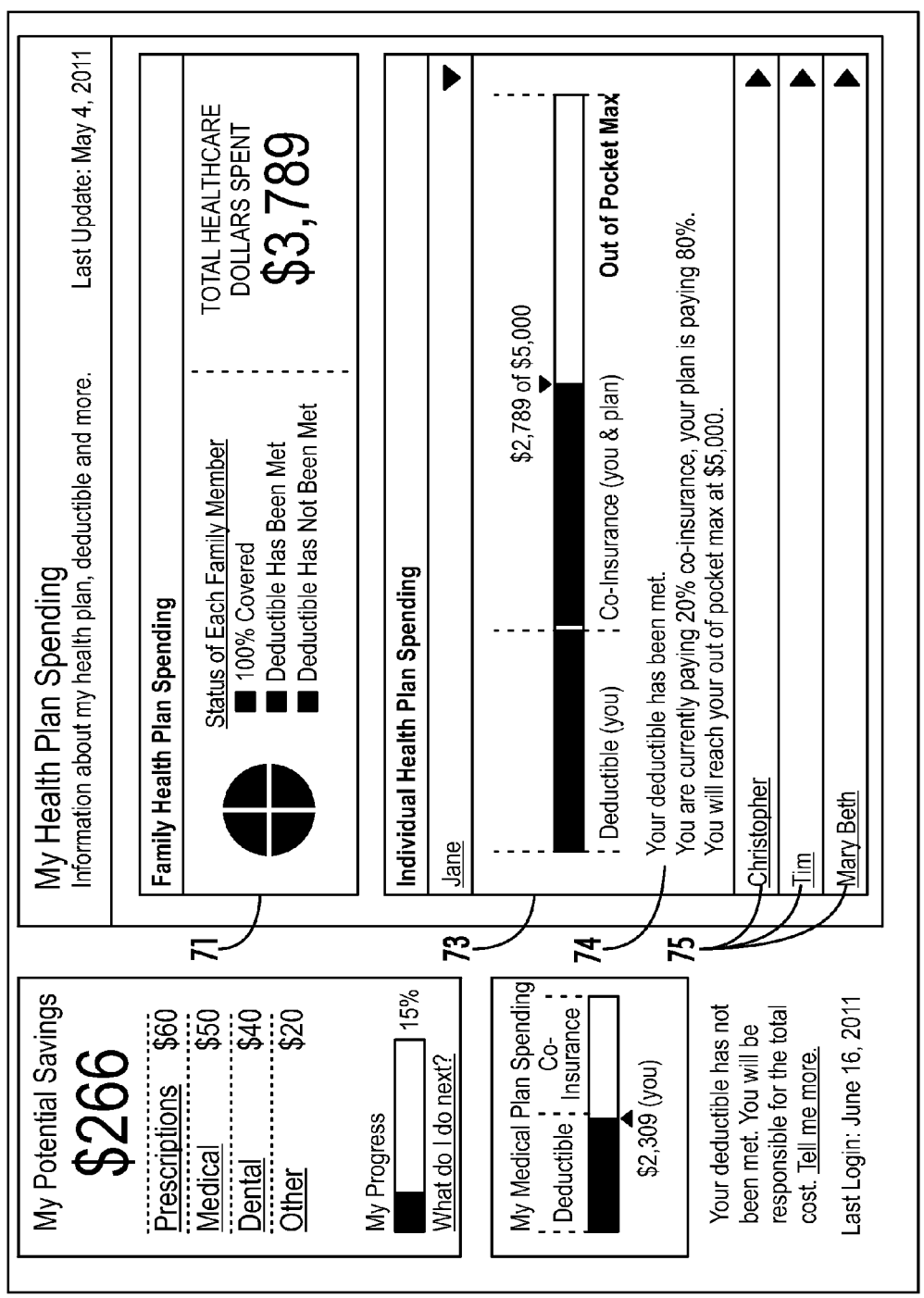
FIG. 7 is a modified screen shot representing a third exemplary graphical user interface field according to the present invention.

FIG. 7 represents a third exemplary display screen 70 for a plan spending details page within the scope of the present invention. This screen 70 may be generated in response to a user query or selection regarding details of a deductible status for an entire family. A first portion 71 refers to chart showing a current status for each individual family member (appropriate shading or coloring may typically be provided but is omitted herein). A second portion 72 includes a dollar value showing a total amount spent towards being fully covered. A third portion 73 includes a breakdown of each individual family member and where they are within the relevant healthcare plan, as represented along a sliding scale from deductible through co-insurance to the out-of-pocket maximum. A fourth portion 74 provides specific plan details, current status, amount spent on healthcare during a current plan year, etc. A fifth portion 75 may provide further information and indicators and/or links to further information and indicators regarding additional family members or associated entities with respect to the healthcare plan and their status.

Figure 8:
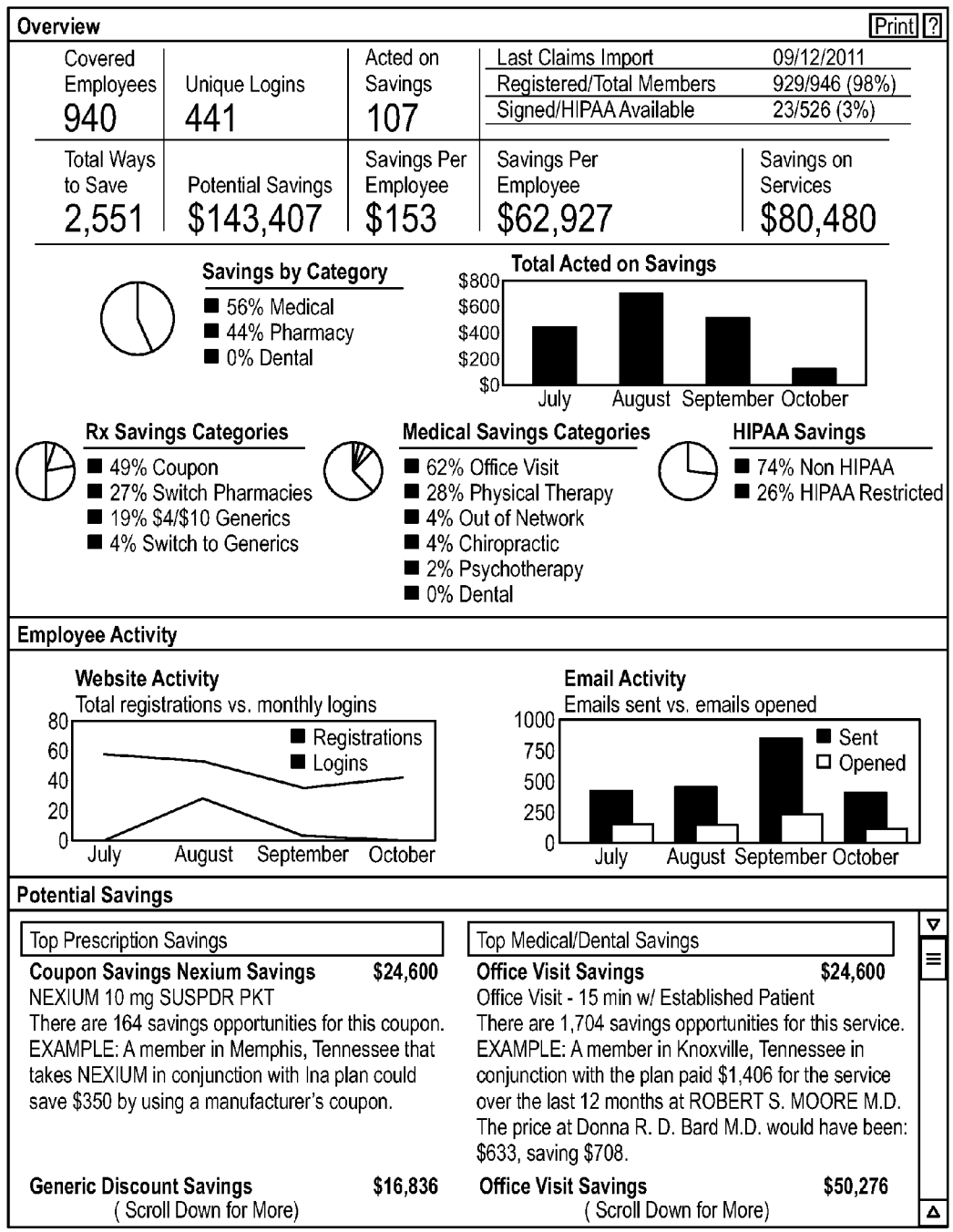
FIG. 8 is a modified screen shot representing a fourth exemplary graphical user interface field according to the present invention.

FIG. 8 represents a fourth exemplary display screen 80 such as may be accessible by for example plan administrators within the scope of the present invention. The interface 80 may be generated to include a general overview of savings incurred to date through the use of the host system and associated methods, savings by category, monitored and recorded activity with respect to plan participants (e.g., employees of the administrator or an employer associated with the administrator), potential savings as yet unrealized, etc.

The previous detailed description has been provided for the purposes of illustration and description. Thus, although there have been described particular embodiments of the present invention of a new and useful "Web-Based System and Method for Health Care Cost Management," it is not intended that such references be construed as limitations upon the scope of this invention except as set forth in the following claims.

What is claimed is:

1. A computer program product tangibly embodied in a non-transitory computer-readable memory medium, the computer program product including program instructions executable by a processor to direct the performance of operations comprising:

obtaining a claim regarding healthcare services from a registered user at a hosted server via a communications network, the claim including healthcare service data associated with said services;

identifying an account associated with the registered user and having user details stored in a database functionally linked to the hosted server;

enabling the registered user to define one or more of the user details as availability criteria comprising one or more of a minimum cost savings threshold and a maximum distance threshold;

extracting details of a healthcare plan associated with the registered user from a database functionally linked to the hosted server;

identifying one or more comparable claims having healthcare service data stored in a database functionally linked to the hosted server, the claims determined as being comparable based on criteria comprising a healthcare provider specialty and service code;

resolving the healthcare service data for the obtained claim against the healthcare service data for the one or more comparable claims to identify available healthcare service options for future occurrences of the same service for the user based on availability criteria comprising one or more of the minimum cost savings threshold and the maximum distance threshold;

generating a graphical user interface field comprising a message effective to notify the user of any identified available options;

enabling the user to provide declined options feedback regarding any one or more available options;

dynamically adjusting one or more of the minimum cost savings threshold and the maximum distance threshold based on the declined options feedback from the user; and responsive to a user request via the graphical user interface associated with one or more of said identified available options, generating a graphical user interface field comprising details for obtaining services associated with the identified available options.

2. The computer program product of claim 1, the program instructions further executable to direct the performance of obtaining healthcare services data from a plurality of third party medical services data sources and storing said healthcare services data from the third party sources in a database functionally linked to the processor and the hosted server, the comparable claims comprising one or more of said third party healthcare services data and data derived from said third party healthcare services data.

3. The computer program product of claim 1, the program instructions further executable to direct the performance of
scoring the identified available claims based on one or more of user-defined preferences associated with the user details, administrator-defined preferences associated with the plan details, quality ratings applied to the sources of the respective service data, predetermined scoring ranges and thresholds, and user profile data generated by the computer program product based on previous activity by the user.

4. The computer program product of claim 3, the predetermined scoring ranges and thresholds relating to one or more of a geographic distance, quality rating and cost.

5. The computer program product of claim 1, the program instructions further executable to direct the performance of generating a graphical user interface field including a financial return report based on input from the user corresponding to an actual difference in price between medical care services.

6. The computer program product of claim 5, the program instructions further executable to direct the performance of generating in response to the user request a graphical user interface field including a map identifying a location and descriptive data associated with each of the one or more identified options.

7. A computer program product tangibly embodied in a non-transitory computer-readable memory medium, the computer program product including program instructions executable by a processor to direct the performance of operations comprising:

obtaining from a healthcare plan administrator a claim regarding healthcare services for a plan participant at a hosted server via a communications network, the claim including healthcare service data associated with said services;

identifying an account associated with the participant and having participant account details stored in a database functionally linked to the hosted server, the participant account details comprising one or more healthcare service option availability criteria;

extracting details of a healthcare plan associated with the administrator and the participant from a database functionally linked to the hosted server;

identifying one or more comparable claims having healthcare service data stored in a database functionally linked to the hosted server, the claims determined as being comparable based on criteria comprising a healthcare provider specialty and service code;

resolving the healthcare service data for the obtained claim against the healthcare service data for the one or more comparable claims to identify available healthcare service options for future occurrences of the same service based on the availability criteria;

generating a graphical user interface field comprising a message effective to notify the participant of any identified available options;

enabling the participant to provide declined options feedback regarding any one or more identified available options;

dynamically generating or adjusting availability criteria comprising one or more of a minimum cost savings threshold and a maximum distance threshold based on the declined options feedback from the participant; and responsive to receiving a request via the graphical user interface from the participant in association with one or more of said identified options, generating a graphical user interface field comprising details for obtaining healthcare services associated with the identified options.

8. The computer program product of claim 7, the program instructions further executable to direct the performance of obtaining healthcare services data from a plurality of third party healthcare services data sources and storing said medical services data from the third party sources in a database functionally linked to the processor and the hosted server, the comparable claims comprising one or more of said third party healthcare services data and data derived from said third party healthcare services data.

9. The computer program product of claim 7, the program instructions further effective to direct the performance of
scoring the identified available claims based on one or more of participant-defined preferences associated with the account details, administrator-defined preferences associated with the plan details, quality ratings applied to the sources of the respective service data, predetermined scoring ranges and thresholds, and profile data generated by the computer program product based on previous activity by the participant.

10. The computer program product of claim 9, the predetermined scoring ranges and thresholds relating to one or more of a geographic distance, quality rating and cost.

11. The computer program product of claim 7, the program instructions further executable to direct the performance of generating a graphical user interface field including a financial return report based on input from the participant corresponding to an actual difference in price between medical care services.

12. The computer program product of claim 11, the program instructions further executable to direct the performance of generating in response to the request by the participant a graphical user interface field including a map identifying a location and descriptive data associated with each of the one or more identified options.

13. A computer program product tangibly embodied in a non-transitory computer-readable memory medium, the computer program product including program instructions executable by a processor to direct the performance of operations comprising:

obtaining from a healthcare plan administrator a claim regarding healthcare services for a plan participant at a hosted server via a communications network, the claim including healthcare service data associated with said services;

identifying an account associated with the participant and having participant account details stored in a database functionally linked to the hosted server;

enabling the participant to define one or more of the participant account details as preferences with respect to one or more of cost, distance and service provider;

extracting details of a healthcare plan associated with the administrator and the participant from a database functionally linked to the processor and the hosted server, the healthcare plan details comprising one or more healthcare service option availability criteria;

identifying one or more comparable claims having healthcare service data stored in a database functionally linked to the hosted server, the claims determined as being comparable based on criteria comprising a healthcare provider specialty and service code;

resolving the healthcare service data for the obtained claim against the healthcare service data for the one or more comparable claims to identify available healthcare service options for future occurrences of the same service for the participant based on the availability criteria;

scoring the identified available claims based on scoring criteria comprising the participant-defined preferences;

generating a graphical user interface field comprising a message effective to notify the participant of identified available options;

enabling the participant to provide declined options feedback regarding any one or more identified available options;

dynamically generating or adjusting one or more of the participant-defined preferences based on the declined options feedback; and responsive to receiving a request from the participant via the graphical user interface in association with one or more of said identified options, generating a graphical user interface field comprising details for obtaining services associated with the identified options.

14. The computer program product of claim 13, the program instructions further executable to direct the performance of obtaining healthcare services data from a plurality of third party healthcare services data sources and store said healthcare services data from the third party sources in a database functionally linked to the processor and the hosted server, the comparable claims comprising one or more of said third party healthcare services data and data derived from said third party healthcare services data.

15. The computer program product of claim 13, the program instructions further executable to direct the performance of scoring the identified available claims based on one or more of administrator-defined preferences associated with the plan details, quality ratings applied to the sources of the respective service data, and predetermined scoring ranges and thresholds.

16. The computer program product of claim 13, the program instructions further executable to direct the performance of generating a graphical user interface field including a financial return report based on input from the participant corresponding to an actual difference in price between medical care services.

17. The computer program product of claim 16, the program instructions further executable to direct the performance of generating in response to the request by the participant a graphical user interface field including a map identifying a location and descriptive data associated with each of the one or more identified available options.

* * * * *